US010653304B2

(12) United States Patent
Matsui et al.

(10) Patent No.: US 10,653,304 B2
(45) Date of Patent: May 19, 2020

(54) ENDOSCOPE AND ENDOSCOPE SYSTEM

(71) Applicant: OLYMPUS CORPORATION, Tokyo (JP)

(72) Inventors: Yasunori Matsui, Hino (JP); Shinji Yamashita, Tachikawa (JP); Yuzuru Tanabe, Niiza (JP); Yuta Matsuno, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/161,218

(22) Filed: Oct. 16, 2018

(65) Prior Publication Data

US 2019/0046022 A1 Feb. 14, 2019

Related U.S. Application Data

(63) Continuation of application No. PCT/JP2017/030787, filed on Aug. 28, 2017.

(30) Foreign Application Priority Data

Sep. 5, 2016 (JP) .................. 2016-172814

(51) Int. Cl.
A61B 1/045 (2006.01)
A61B 1/06 (2006.01)
(Continued)

(52) U.S. Cl.
CPC .......... A61B 1/045 (2013.01); A61B 1/00009 (2013.01); A61B 1/0661 (2013.01);
(Continued)

(58) Field of Classification Search
CPC . A61B 1/045; A61B 1/00009; A61B 1/00059; A61B 1/06; A61B 1/07
See application file for complete search history.

(56) References Cited

U.S. PATENT DOCUMENTS 4,953,539 A * 9/1990 Nakamura ......... A61B 1/00177
348/E5.029
5,408,263 A * 4/1995 Kikuchi ............ A61B 1/00059
348/223.1
(Continued)

FOREIGN PATENT DOCUMENTS

JP H03-121032 A 5/1991
JP 2013-248149 A 12/2013
(Continued)

OTHER PUBLICATIONS

International Search Report dated Oct. 3, 2017 issued in PCT/JP2017/030787.
English Abstract of JP 2014-094316 dated May 22, 2014.

Primary Examiner — Obafemi O Sosanya
(74) Attorney, Agent, or Firm — Scully, Scott, Murphy & Presser, P.C.

(57) ABSTRACT

An endoscope includes: an illuminator configured to guide illumination light from a light source capable of emitting the illumination light intermittently and apply the illumination light to an object; an imaging element including a light receiver where multiple pixels configured to receive light and perform photoelectric conversion to generate electric signals are arranged in a two-dimensional matrix, and a reader configured to sequentially read the electric signals per horizontal line from each of the multiple pixels; a generator configured to, based on a first vertical synchronization signal that is input from an external processor and reference timing of exposure of the imaging element with the illumination light, generate a second vertical synchronization signal for controlling timing at which the reader reads the electric signal; and an imaging controller configured to cause the reader to read the electric signals sequentially according to the second vertical synchronization signal.

6 Claims, 7 Drawing Sheets

(51) Int. Cl.
  *A61B 1/07*    (2006.01)
  *G02B 23/24*   (2006.01)
  *G02B 23/26*   (2006.01)
  *A61B 1/00*    (2006.01)

(52) U.S. Cl.
  CPC ............ *G02B 23/24* (2013.01); *G02B 23/26* (2013.01); *A61B 1/00096* (2013.01); *A61B 1/0669* (2013.01); *A61B 1/07* (2013.01); *G02B 23/2407* (2013.01)

(56)          References Cited

U.S. PATENT DOCUMENTS

| | | | | |
|---|---|---|---|---|
| 2008/0079814 | A1* | 4/2008 | Nobuoka | ............... H04N 5/772 |
| | | | | 348/208.99 |
| 2013/0265403 | A1* | 10/2013 | Okawa | .................... A61B 1/04 |
| | | | | 348/76 |
| 2013/0329028 | A1* | 12/2013 | Saito | ...................... A61B 1/045 |
| | | | | 348/68 |
| 2014/0275764 | A1* | 9/2014 | Shen | .................... A61B 1/0661 |
| | | | | 600/103 |
| 2015/0022647 | A1* | 1/2015 | Takei | ................. A61B 1/00186 |
| | | | | 348/70 |

FOREIGN PATENT DOCUMENTS

| | | |
|---|---|---|
| JP | 5724006 B2 | 5/2015 |
| WO | WO 2015/114906 A1 | 8/2015 |

\* cited by examiner

ENDOSCOPE AND ENDOSCOPE SYSTEM

CROSS-REFERENCE TO RELATED APPLICATION

This application is a continuation of PCT International Application No. PCT/JP2017/030787 filed on Aug. 28, 2017 which claims the benefit of priority from Japanese Patent Application No. 2016-172814, filed on Sep. 5, 2016, the entire contents of which are incorporated herein by reference.

BACKGROUND

1. Technical Field

The present disclosure relates to an endoscope that capture in-vivo images of a subject to generate image data on the subject and to an endoscope system.

2. Related Art

In the related art, in the field of medicine, endoscope systems each including an endoscope to perform in-vivo observation on a subject, such as a patient, are used. An endoscope applies illumination light from the tip of an insertion unit that is inserted into a subject and receives the reflected light of the illumination light with an imaging element, thereby capturing in-vivo images. A processor (processing device) to which the endoscope is connected performs predetermined image processing on the in-vivo images that are captured by the imaging unit of the endoscope as described above.

In such endoscope systems, a technology using a complementary metal oxide semiconductor (CMOS) image sensor as the imaging element that is arranged at the tip of the endoscope and using a light source device including a solid light source that can be driven intermittently, such as a light emitting diode (LED) or a laser diode, as a light source device for illuminating an object is known (see Japanese Patent No. 5724006). According to the technology, the processor outputs a vertical synchronization signal to the endoscope and the light source device to cause the light source device to execute pulse width modulation (PWM) light adjustment during a blank period of the imaging element, thereby adjusting the luminance of the illumination light.

SUMMARY

In some embodiments, an endoscope includes: an illuminator configured to guide illumination light from a light source capable of emitting the illumination light intermittently and apply the illumination light to an object; an imaging element including a light receiver where multiple pixels configured to receive light and perform photoelectric conversion to generate electric signals are arranged in a two-dimensional matrix, and a reader configured to sequentially read the electric signals per horizontal line from each of the multiple pixels; a generator configured to, based on a first vertical synchronization signal that is input from an external processor and reference timing of exposure of the imaging element with the illumination light, generate a second vertical synchronization signal for controlling timing at which the reader reads the electric signal; and an imaging controller configured to cause the reader to read the electric signals sequentially according to the second vertical synchronization signal.

In some embodiments, an endoscope system includes: the endoscope; the light source configured to intermittently emit the illumination light; and a processor configured to perform predetermined image processing on the electric signals that are generated by the endoscope. The light source is configured to perform PWM light adjustment per frame of the imaging element.

The above and other features, advantages and technical and industrial significance of this invention will be better understood by reading the following detailed description of presently preferred embodiments of the disclosure, when considered in connection with the accompanying drawings.

DETAILED DESCRIPTION

Figure 1:
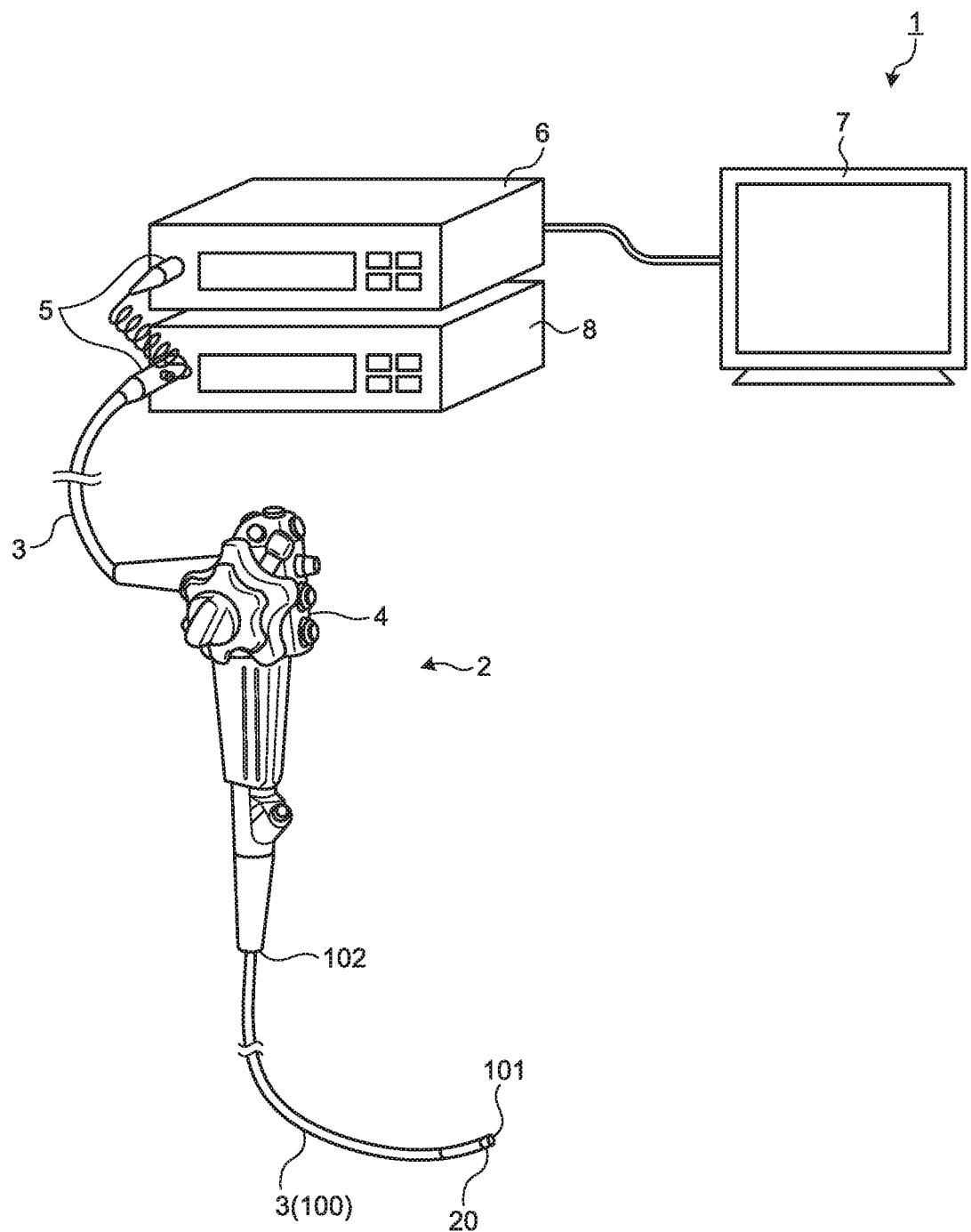
FIG. 1 is a schematic diagram schematically illustrating an overall configuration of an endoscope system according to a first embodiment of the disclosure.

Endoscope systems each including an endoscope whose tip is configured to be inserted into a subject will be described below as modes for carrying out the disclosure ("embodiments" below). The embodiments do not limit the invention. In description of the drawings, the same components are denoted with the same reference numeral and described. Note that the drawings are schematic and thus the relation between the thickness and width of each member, the ratio of each member, etc., are different from the real ones. The drawings contain components that are different in size and ratio between the drawings.

First Embodiment

Configuration of Endoscope System

FIG. 1 is a schematic diagram schematically illustrating an overall configuration of an endoscope system according to a first embodiment of the disclosure. An endoscope system 1 illustrated in FIG. 1 includes an endoscope 2 (scope) that captures an in-vivo image of a subject and generates image data, a processor 6 (control device) that performs predetermined image processing on the image data that is generated by the endoscope 2, a display device 7 that displays the image corresponding to the image data on which the processor has performed the image processing, and a light source device 8 that supplies illumination light to the endoscope 2.

The endoscope 2 includes a transmission cable 3, an operation unit 4 and a connector unit 5. The endoscope 2 inserts an insertion unit 100 that is a part of the transmission cable 3 into the body cavity of the subject to capture in-vivo images of the subject and outputs the image data (image signals) to the processor 6. In the endoscope 2, an imaging unit 20 (imaging device) that captures in-vivo images is provided is provided on the side of a tip part 101 of the insertion unit 100 that is one end of the transmission cable 3 and that is configured to be inserted into the body cavity of the subject. In the endoscope 2, the operation unit 4 that receives various operations on the endoscope 2 is provided on the side of a base end 102 of the insertion unit 100. The image data that is captured by the imaging unit 20 is output to the connector unit 5 via the transmission cable 3 having a length of, for example, few meters.

The transmission cable 3 connects the endoscope 2 and the connector unit 5 and connects the endoscope 2 and the light source device 8. The transmission cable 3 transmits the image data that is generated by the imaging unit 20 to the connector unit 5. The transmission cable 3 includes cables cable, optical fibers, or the like.

The connector unit 5 is connected to the endoscope 2, the processor 6 and the light source device 8, performs predetermined signal processing on the image data that is output by the connected endoscope 2, converts the analog image data into digital image data (A/D conversion) and output the digital image data to the processor 6.

The processor 6 performs predetermined image processing on the image data that is input from the connector unit 5 and outputs the processed image data to the display device 7. The processor 6 also performs overall control on the entire endoscope system 1.

The display device 7 displays the images corresponding to the image data on which the processor 6 has performed the image processing. The display device 7 displays various types of information on the endoscope system 1. The display device 7 includes a display panel, such as a liquid or electro luminescence (EL) display panel.

The light source device 8 intermittently applies illumination light to the subject from the side of the tip part 101 of the insertion unit 100 of the endoscope 2 via the connector unit 5 and the transmission cable 3.

Figure 2:
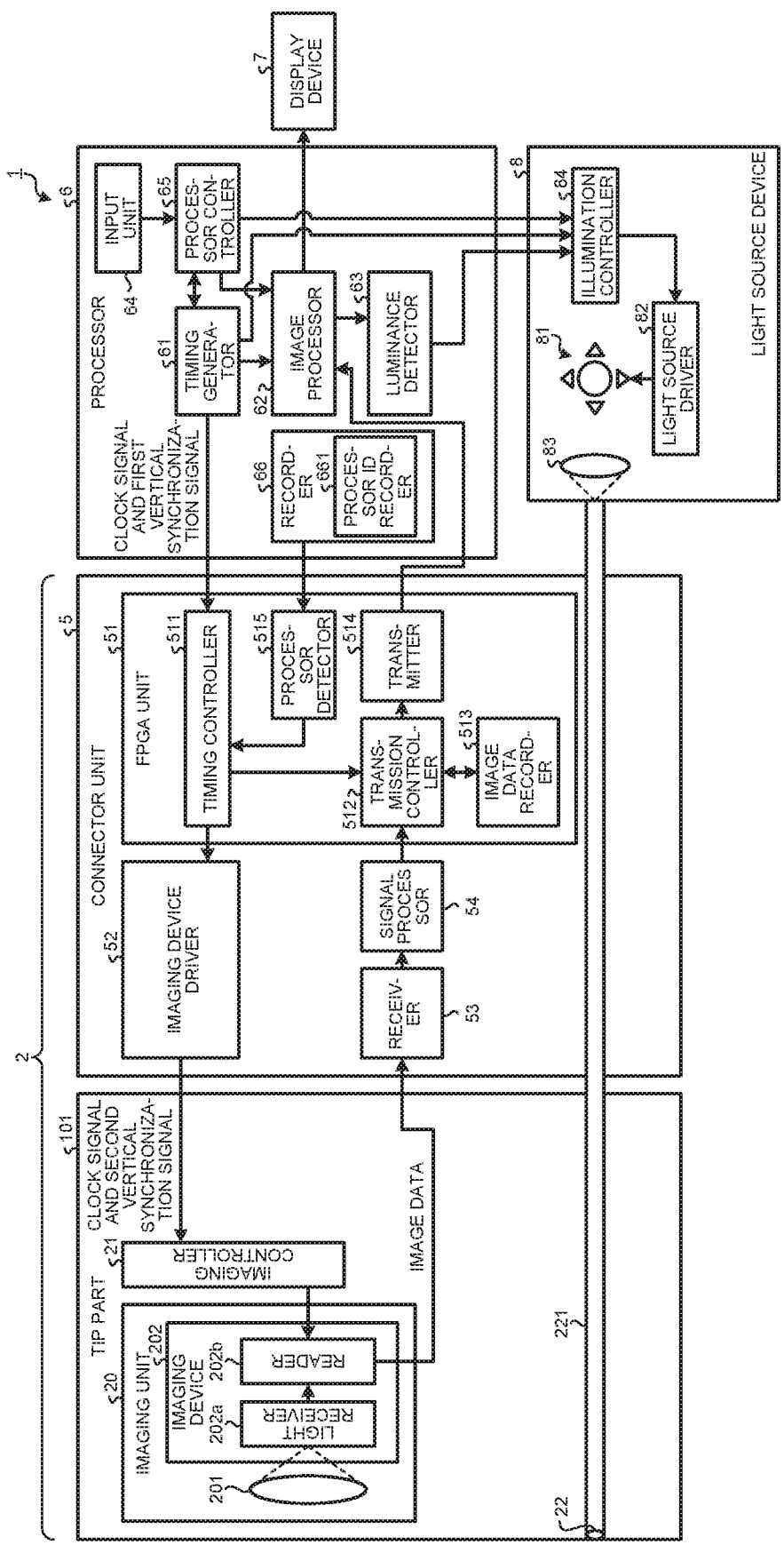
FIG. 2 is a block diagram illustrating relevant functions of the endoscope system according to the first embodiment.

FIG. 2 is a block diagram illustrating relevant functions of the endoscope system 1. With reference to FIG. 2, details of each component of the endoscope system 1 and a route of electric signals in the endoscope system 1 will be described.

Configuration of Endoscope

First of all, a configuration of the endoscope 2 will be described. The endoscope 2 illustrated in FIG. 2 includes the imaging unit 20, an imaging controller 21, an illuminator 22, the transmission cable 3, and the connector unit 5.

The imaging unit 20 captures in-vivo images of a subject and generates image data. The imaging unit 20 includes an optical system 201 and an imaging element 202.

The optical system 201 includes at least one lens, a prism, etc. The optical system 201 forms an object image on a light receiving surface of the imaging element 202.

The imaging element 202 receives the light of the object image that is formed by the optical system 201 and performs photoelectric conversion to generate image data and outputs the image data to the connector unit 5 via the transmission cable 3. The imaging element 202 includes an image sensor, such as a complementary metal oxide semiconductor (CMOS). The imaging element 202 includes a light receiver 202a where multiple pixels are arranged in a two-dimensional matrix and a reader 202b. The multiple pixels are configured to receive light and perform photoelectric conversion to generate electric signals (image data). The reader 202b is configured to sequentially read the electric signal from each of the multiple pixels per each horizontal line. The imaging element 202 outputs the image data to the connector unit 5 via the transmission cable 3 under the control of the imaging controller 21.

The imaging controller 21 causes the reader 202b to sequentially read image data per horizontal line of the light receiver 202a and output the image data in a light-blocking period (off period) of the illuminator 22 based on a clock signal and a second vertical synchronization signal (Csync) that are input from the connector unit 5, which will be described below, via the transmission cable 3.

The illuminator 22 guides the illumination light that is emitted from the light source device 8 and applies the illumination light to the subject. The illuminator 22 is realized by using a light guide 221 including glass fibers, or the like, and an illumination lens, or the like.

The connector unit 5 includes a field programmable gate array (FPGA) unit 51, an imaging device driver 52, a receiver 53 and a signal processor 54.

The FPGA unit 51 includes a timing controller 511, a transmission controller 512, an image data recorder 513, a transmitter 514 and a processor detector 515.

Based on the clock signal and a first vertical synchronization signal that are input from the processor 6 to be described below, and on a reference timing of exposure of the imaging element 202 with the illumination light that is emitted by the light source device 8, the timing controller 511 generates the second vertical synchronization signal for controlling the timing at which the reader 202b reads an electric signal from the light receiver 202a. Specifically, based on the clock signal and the first vertical synchronization signal that are input from the processor 6 to be described below, and on the reference timing of exposure of the imaging element 202 with the illumination light that is emitted by the light source device 8, the timing controller 511 generates the second vertical synchronization signal and a clock signal for driving the imaging element 202 such that the timing of end of the illumination light that is emitted by the light source device 8 and the timing at which the reader 202b reads an electric signal (image data) from pixels of the light receiver 202a match and outputs the second vertical synchronization signal and the clock signal to the imaging device driver 52. More specifically, the timing controller 511 generates the second vertical synchronization signal that is delayed by a predetermined time with respect to the clock signal and the first vertical synchronization signal that are input from the processor 6. The timing controller 511 generates the second vertical synchronization signal based on the result of detection performed by the processor detector 515, which will be described below, and the first vertical synchronization signal. The timing controller 511 outputs the clock signal and the first vertical synchronization signal that are input from the processor 6, which will be described below, to the transmission controller 512. In the first embodiment, the timing controller 511 functions as a generator.

The transmission controller 512 outputs the image data that is input via the receiver 53 and the signal processor 54 to the image data recorder 513 and causes the image data recorder to temporarily record the image data and, based on the clock signal and the first vertical synchronization signal, which are input from the timing controller 511, causes the transmitter 514 to transmit the image data that the image data recorder 513 records temporarily to the processor 6 at timing synchronized with the first vertical synchronization signal that is input from the processor 6.

The transmitter 514 outputs the image data that is input from the transmission controller 512 to the processor 6. Specifically, under the control of the transmission controller 512, the transmitter 514 transmits the image data that the image data recorder 513 records temporarily to the processor 6.

The processor detector 515 detects the type of the processor 6 to which the endoscope 2 is connected and outputs the result of the detection to the timing controller 511. Specifically, the processor detector 515 acquires processor ID information that identifies the processor 6 and that is recorded by a processor ID recorder 661 of the processor 6 to be described below and, based on the acquired processor ID information, detects the type of the processor 6. The processor ID information contains the form of the processor ID, the light source system (for example, PWM light adjustment, or the like), the illumination system (for example, sequential lighting or simultaneous lighting), the timing of the first vertical synchronization signal and the timing of the clock signal.

The imaging device driver 52 outputs the clock signal and the second vertical synchronization signal, which are input from the timing controller 511 of the FPGA unit 51, to the imaging unit 20 via the transmission cable 3, thereby driving the imaging unit 20.

The receiver 53 receives the image data that is output from the imaging element 202 and outputs the image data to the signal processor 54.

The signal processor 54 performs analog signal processing, such as signal amplitude amplification, on the image data that is input from the receiver 53 and outputs the processed image data to the FPGA unit 51.

Configuration of Processor

A configuration of the processor 6 will be described. The processor 6 includes a timing generator 61, an image processor 62, a luminance detector 63, an input unit 64, a processor controller 65 and a recorder 66.

The timing generator 61 generates the clock signal (for example, 27-MHz clock signal) that servers as a reference of operations of each component of the endoscope 2 and the first vertical synchronization signal representing timing of start of each frame of image data and outputs the clock signal and the first vertical synchronization signal to the timing controller 511, the image processor 62, the processor controller 65 and the light source device 8, which will be described below.

The image processor 62 performs image processing, such as synchronization processing, white balance (WB) adjustment processing, gain adjustment processing, gamma correction processing, digital/analog (D/A) conversion processing and format conversion processing, and outputs the processed image data to each of the luminance detector 63 and the display device 7.

The luminance detector 63 detects an amount of light that is emitted by the light source device 8 based on the image data that is input from the image processor 62 and outputs the result of the detection to the light source device 8. Specifically, the luminance detector 63 determines whether the object has a high luminance or a low luminance based on the image data that is input from the image processor 62 and, after calculating an amount of light according to the result of the determination, outputs the result of the calculation to the light source device 8. More specifically, the luminance detector 63 determines whether the luminance of the image corresponding to the image data that is input from the image processor 62 (for example, an average or standard deviation of luminance values) is equal to or higher than a pre-set threshold. The luminance detector 63 determines that the object has a high luminance when the luminance is equal to or higher than the threshold and meanwhile determines that the object has a low luminance when the luminance is lower than the threshold. After calculating an amount of light corresponding to the result of the determination, the luminance detector 63 outputs the result of the calculation to the light source device 8.

The input unit 64 receives inputs of various operations relating to the endoscope system 1. The input unit 64 includes, for example, a cross switch, a push button, etc.

The processor controller 65 includes, for example, a central processing unit (CPU) and performs overall control on each component of the endoscope system 1.

The recorder 66 includes a volatile memory, a non-volatile memory, etc., and records various types of information of the processor 6. The recorder 66 includes the processor ID recorder 661 that records processor ID information that identifies the processor 6.

Configuration of Light Source Device

A configuration of the light source device 8 will be described. The light source device 8 includes a light source 81, a light source driver 82, a condenser lens 83, and an illumination controller 84.

The light source 81 emits white light. The white light that is emitted by the light source 81 is applied externally from the tip part 101 of the endoscope 2 via the condenser lens 83 and the light guide 221. The light source 81 includes a light emitting diode (LED).

The light source driver 82 supplies power to the light source 81 at predetermined intervals to perform pulse width modulation (PWM) light adjustment on the light source 81.

The condenser lens 83 condenses the white light that is emitted by the light source 81 and emits the condensed light to the light guide 221. The condenser lens 83 includes at least one lens.

The illumination controller 84 includes a CPU, etc., and controls the light source driver 82 based on the clock signal and the first vertical synchronization signal, which are input from the timing generator 61, thereby controlling the amount of light in PWM light adjustment on the light source 81. Specifically, the illumination controller 84 controls the light source driver 82 according to the calculation result that is input from the luminance detector 63. More specifically, the illumination controller 84 controls the light source driver 82 based on the information on the amount of light, which is input from the luminance detector 63, thereby controlling the amount of light in PWM light adjustment performed by the light source 81.

Operations of Endoscope

Figure 3:
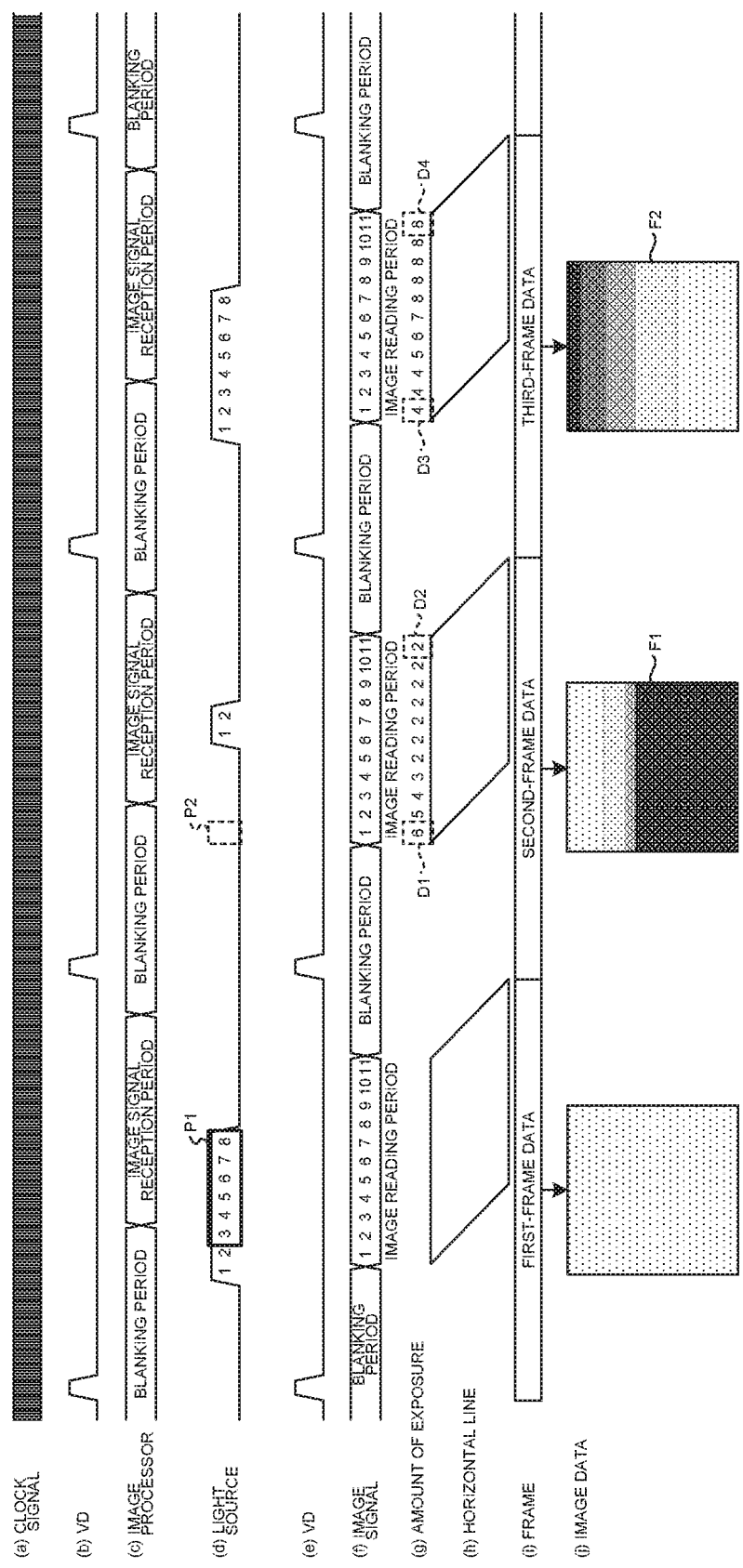
FIG. 3 is a diagram illustrating a timing chart schematically representing operations performed when a endoscope system in the related art is in a low-luminance mode.
Figure 4:
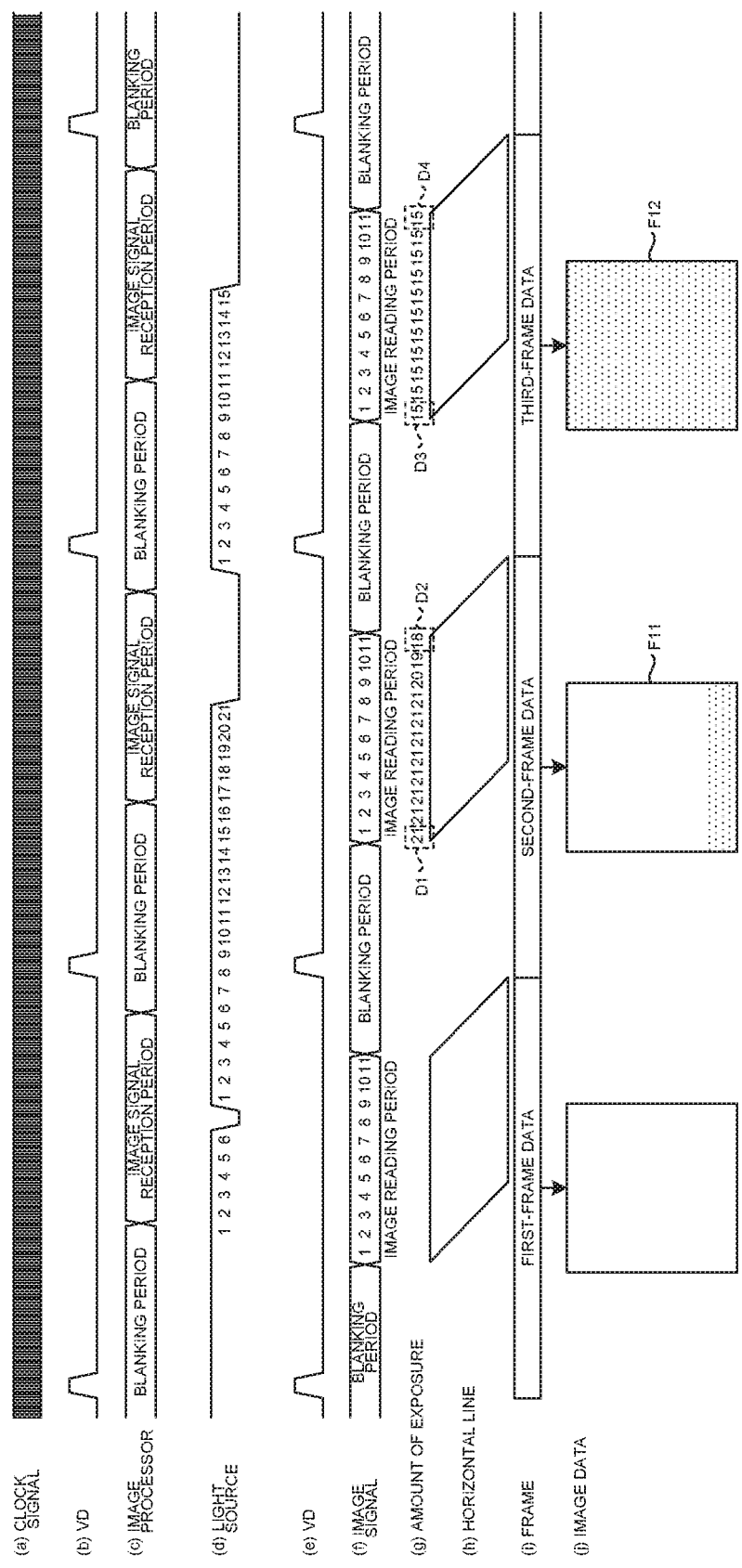
FIG. 4 is a diagram illustrating a timing chart schematically representing operations performed when a endoscope system in the related art is in a high-luminance mode.

Operations of the endoscope 2 will be described. Operations of a endoscope system in the related art will be described and then operations of the endoscope system 1 according to the embodiment will be described below. FIG. 3 is a diagram illustrating a timing chart schematically representing operations performed when the endoscope system in the related art is in a low-luminance mode. FIG. 4 is a diagram illustrating a timing chart schematically representing operations performed when the endoscope system in the related art is in a high-luminance mode. In FIGS. 3 and 4, from the top, (a) represents a clock signal, (b) represents timing of a vertical synchronization signal (VD), (c) represents operations of the image processor, (d) represents timing of light adjustment performed by the light source device, (e) represents a vertical synchronization signal, (f) represents timing of reading image data (image signal), (g) represents amounts of exposure of pixels, (h) represents timing of reading pixel horizontal lines, (i) represents timing of frames of image data and (j) represents images of image data. FIGS. 3 and 4 will be described, assuming that there are 11 horizontal lines schematically.

Operation Timing in the Related Art

First of all, operations performed by the endoscope system in the related art when the luminance is low will be described. As illustrated in FIG. 3, in the case where the light source is performing PWM light adjustment in a low-illuminance mode, when the endoscope system in the related art captures images of an object by a rolling shutter method using a CMOS imager as an imaging element, a mismatch between light adjustment timing and timing of reading a video signal causes a large luminance difference in the images corresponding to image data that is generated by the imaging element.

Specifically, as illustrated in FIG. 3, in the endoscope system in the related art, in the second-frame data, in an exposure period after the first-line image data is read in the first-frame data, the amount of exposure of the first line in the previous frame (see an area P1) is "6", the amount of exposure of the first line in the current frame (see an area P2) is "0" and thus an accumulated exposure amount D1 is "6". On the other hand, in the endoscope system in the related art, in the second-frame data, in the exposure period after the 11-th-line image data in the first-frame data is read, the amount of exposure of the 11-th line in the previous frame is "0", the amount of exposure of the 11-th line in the current frame is "2" and thus an accumulated exposure amount D2 is "2". As a result, a large luminance difference (for example, a luminance variability of 67%) occurs in an image F1.

In the endoscope system in the related art, in the third-frame data, in an exposure period after the first-line image data is read in the second-frame data, the amount of exposure of the first line in the previous frame is "2", the amount of exposure of the first line in the current frame is "2" and thus an accumulated exposure amount D3 is "4". On the other hand, in the endoscope system in the related art, in the third-frame data, in an exposure period after the first-line image data is read in the second-frame data, the amount of exposure of the 11-th line in the previous frame is "0", the amount of exposure of the 11-th line in the current frame is "8" and thus an accumulated exposure amount D4 is "8". As a result, a large luminance difference occurs in an image F2.

Operations performed by the endoscope system in the related art when the luminance is high will be described. As illustrated in FIG. 4, in the endoscope system in the related art, in the second-frame data, in an exposure period after the first-line image data is read in the first-frame data, the amount of exposure of the first line in the previous frame is "13", the amount of exposure of the first line in the current frame is "8" and thus the accumulated exposure amount D1 is "21". On the other hand, in the endoscope system in the related art, in the second-frame data, in an exposure period after the 11-th-line image data is read in the first-frame data, the amount of exposure of the 11-th line in the previous frame is "4", the amount of exposure of the 11-th line in the current frame is "14" and thus the accumulated exposure amount D2 is "18". This results in an image F11 (for example, a luminance variability of 14%) at a level where the user cannot recognize.

In the endoscope system in the related art, in the third-frame data, in an exposure period after the first-line image data is read in the second-frame data, the amount of exposure of the first line in the previous frame is "6", the amount of exposure of the first line in the current frame is "9" and thus the accumulated exposure amount D3 is "15". On the other hand, in the endoscope system in the related art, in the third-frame data, in an exposure period after the first-line image data is read in the second-frame data, the amount of exposure of the 11-th line in the previous frame is "0", the amount of exposure of the 11-th line in the current frame is "15" and thus the accumulated exposure amount D4 is "15". This results in an image F12 (for example, a luminance variability of 0%).

Operation Timing of Endoscope System

Figure 5:
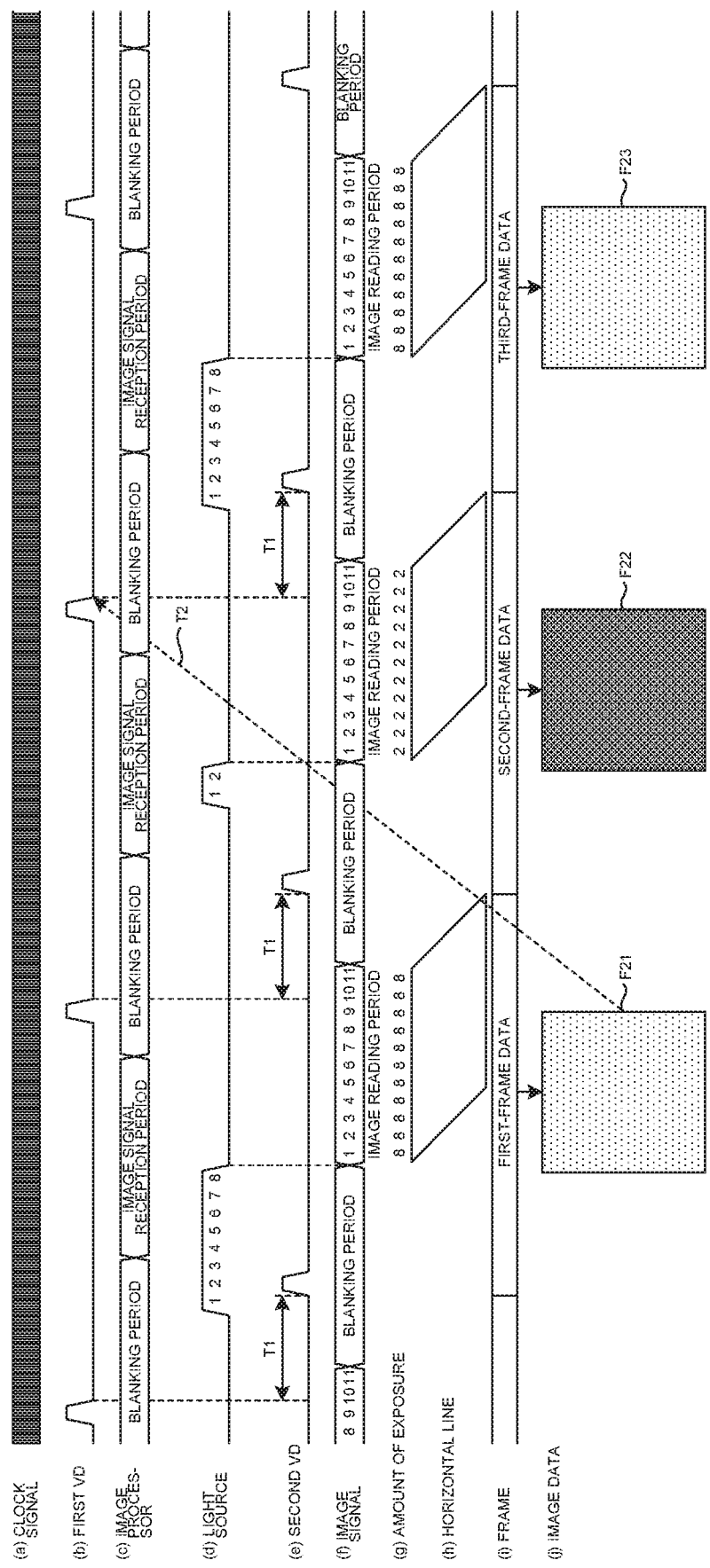
FIG. 5 is a diagram illustrating a timing chart schematically representing operations performed when the endoscope system according to the first embodiment of the invention is in the low-luminance mode.
Figure 6:
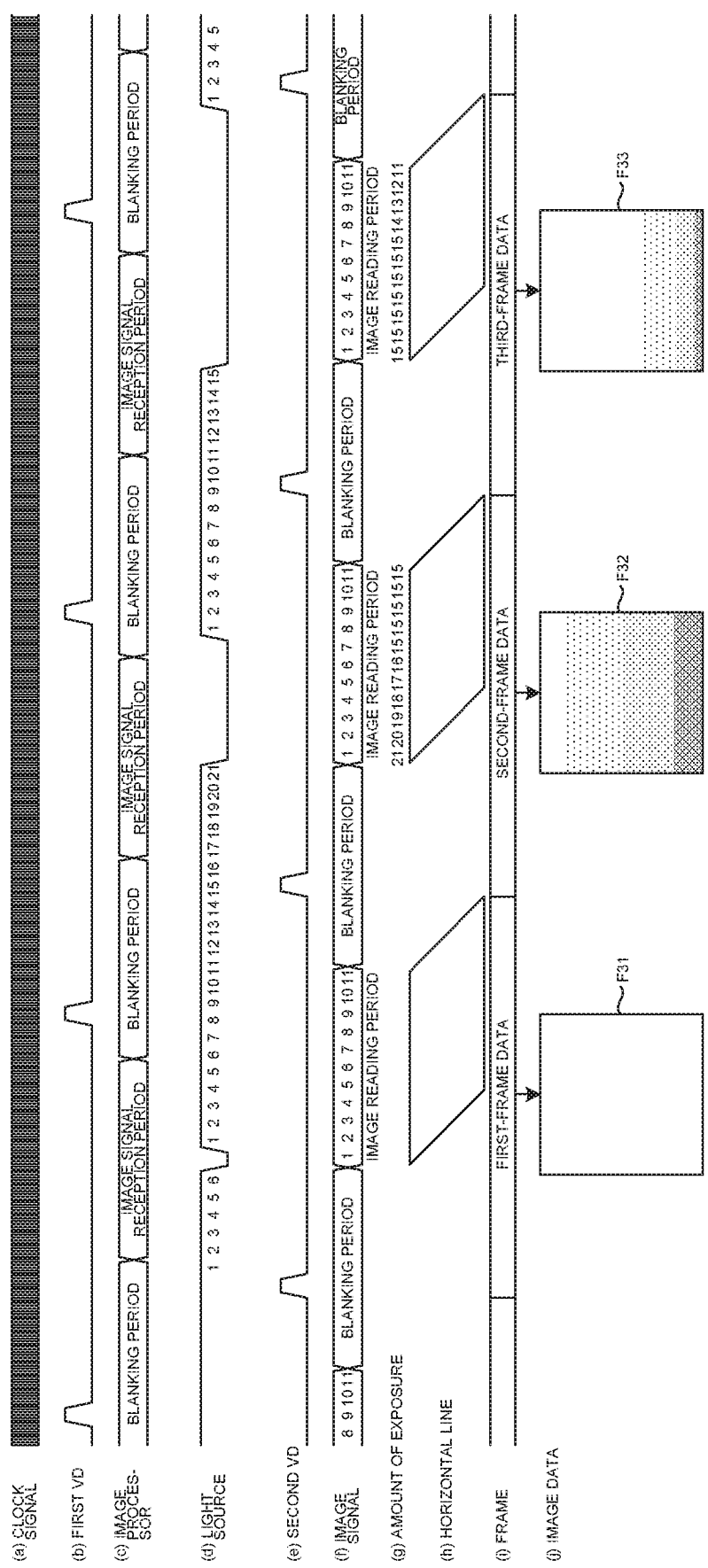
FIG. 6 is a diagram illustrating a timing chart schematically representing operations performed when the endoscope system according to the first embodiment of the invention is in the high-luminance mode.

Operation timing of the endoscope system 1 according to the first embodiment will be described. FIG. 5 is a diagram illustrating a timing chart schematically representing operations performed when the endoscope system 1 is in the low-luminance mode. FIG. 6 is a diagram illustrating a timing chart schematically representing operations performed when the endoscope system 1 is in the high-luminance mode. In FIGS. 5 and 6, from the top, (a) represents a clock signal, (b) represents timing of a first vertical synchronization signal (first VD), (c) represents operations of the image processor, (d) represents timing of light adjustment performed by the light source device, (e) represents a second vertical synchronization signal (second VD), (f) represents timing of reading an image signal, (g) represents amounts of exposure of pixels, (h) represents timing of reading horizontal line pixels, (i) represents timing of frames of image data and (j) represents images of image data. FIGS. 5 and 6 will be described, assuming that there are 11 horizontal lines schematically. The low-luminance mode is a mode where the object has a high luminance (the image on the display device 7 is bright) and the read period includes only a constant time of an off period during which lighting by PWM light adjustment is not performed. Furthermore, the high-luminance mode is a mode where the object has a low luminance (the image on the display device 7 is very dark) and lighting by PWM light adjustment (sequential illumination) is performed even in a reading period. In other words, timing of start of illumination light that is emitted by the light source device 8 is a time when the light source device 8 starts lighting with illumination light when performing lighting with illumination light by PWM light adjustment for only a constant period. Furthermore, the timing of end of illumination light that is emitted by the light source device 8 is a time when the light source device 8 turns off illumination light after performing lighting with illumination light by PWM light adjustment for a constant period.

First of all, operations performed when the endoscope system 1 is in the low-luminance mode will be described. Based on the first vertical synchronization signal that is input from the timing generator 61, the timing controller 511 generates a second vertical synchronization signal representing timing of start of timing of exposure of one frame of the imaging element 202 in the exposure period of the light receiver 202a. Specifically, as illustrated in FIG. 5, the timing controller 511 generates the second vertical synchronization signal such that the reader 202b starts reading image data from the light receiver 202a from a time point that is delayed by a predetermined time T1 with respect to the first vertical synchronization signal, which is a time point when the illuminator 22 starts turning off lighting. Accordingly, in the first-frame data, the imaging controller 21 causes the reader 202b to sequentially read image data from the light receiver 202a during a period in which the illuminator 22 is off according to the second vertical synchronization signal and the clock signal that are input from the timing controller 511. Specifically, the imaging controller 21 causes the reader 202b to sequentially read image data from the light receiver 202a from the time point when the illuminator 22 ends emitting illumination light. As a result, the amount of exposure (the exposure amount is "8") of each horizontal line of the light receiver 202a is equalized and the illumination light generated by the illuminator 22 is not applied during a video reading period and this enables generation of an image F21 without luminance. The transmission controller 512 causes the transmitter 514 to transmit the image data of the image F21, which is recorded in the image data recorder 513, in synchronization with the first vertical synchronization signal T2 of the next frame. Accordingly, even when the vertical synchronization signals of the endoscope 2 and the processor 6 are different from each other, the transmitter 514 transmits the image data at the timing corresponding to the first vertical synchronization signal of the processor 6, thereby enabling appropriate image processing in the processor 6.

Subsequently, as illustrated in FIG. 5, in the second-frame data, the imaging controller 21 causes the reader 202b to sequentially read image data from the light receiver 202a in an period in which the illuminator 22 is off according to the second vertical synchronization signal and the clock signal that are input from the timing controller 511. Specifically, the imaging controller 21 causes the reader 202b to sequentially read image data from the light receiver 202a from a time point when the illuminator 22 ends emitting illumination light. As a result, the amount of exposure amount (the exposure amount is "2") of each horizontal line of the light receiver 202a is equalized and the illumination light generated by the illuminator 22 is not applied during a video reading period and this enables generation of an image F22 without luminance. Furthermore, as represented in images F21, F22 and F23 illustrated in FIG. 5, even when the amount of light in PWM light adjustment by the light source device 8 changes, no luminance difference occurs in each frame of image data. As described above, images without luminance difference are generated in the low-luminance mode.

Furthermore, according to FIG. 5, the transmission controller 512 causes the image data recorder 513 to temporarily record image data that is read per horizontal line from the reader 202b and, according to the first vertical synchronization signal that is input from the timing generator 61 via the timing controller 511, causes the transmitter 514 to transmit the image data that is recorded temporarily in the image data recorder 513. Accordingly, even when the timing of the first vertical synchronization signal of the processor 6 and the timing of the second vertical synchronization signal of the endoscope 2 differ from each other, it is possible to transmit the image data at the timing corresponding to the processor 6 and this enables interchangeability between the processor 6 and the endoscope 2.

Operations performed when the endoscope system 1 is in the high-luminance mode will be described. As illustrated in FIG. 6, based on the first vertical synchronization signal that is input from the timing generator 61, the timing controller 511 generates the second vertical synchronization signal representing timing of start of exposure of one frame of the imaging element 202 in an exposure period of the light receiver 202a. Specifically, as illustrated in FIG. 6, the timing controller 511 generates the second vertical synchronization signal such that the reader 202b starts reading image data from the light receiver 202a at a time point that is delayed by a predetermined time with respect to the first vertical synchronization signal, which is a time point at which the illuminator 22 ends illumination. Accordingly, in the first-frame data, the imaging controller 21 causes the reader 202b to sequentially read image data from the light receiver 202a according to the second vertical synchronization signal and the clock signal that are input from the timing controller 511. As a result, in the read period, even when a luminance difference occurs among images F31, F32 and F33 due to variation in the amount of exposure per frame, the average of the amounts of exposure of the frames is large with respect to the amount of variation in light adjustment among the frames and thus it is possible to keep the luminance difference in each image low.

According to the above-described first embodiment of the disclosure, the timing controller 511 generates the second vertical synchronization signal for controlling the timing at which the reader 202b reads an electric signal based on the first vertical synchronization signal and the reference timing of exposure of the imaging element 202 with illumination light, which is input from the processor 6, and the imaging controller 21 causes the reader 202b to read electric signals sequentially in a period in which the illuminator 22 is off according to the second vertical synchronization signal. Thus, it is possible to prevent occurrence of a luminance difference in an image in the low-luminance mode regardless of the type of the processor 6 to be connected.

According to the first embodiment of the disclosure, the timing controller 511 generates the second vertical synchronization signal that is delayed by the predetermined time with respect to the first vertical synchronization signal that is input from the processor 6. Thus, it is possible to prevent occurrence of a luminance difference in an image regardless of the type of the type of the processor 6 to be connected.

According to the first embodiment of the disclosure, the transmission controller 512 causes the transmitter 514 to transmit electric signals (image data) of one frame that is recorded in the image data recorder 513 in synchronization with the first vertical synchronization signal. Thus, it is possible to transmit the image data corresponding to the type of the processor 6 to be connected.

In the first embodiment of the disclosure, the image sensor of a type in which the image read period is set after the blanking period (all-pixel exposure period) in an one-frame period of the imaging element 202 according to the rise of the first vertical synchronization signal. Alternatively, an image sensor of a type in which a blanking period (all-pixel exposure period) is provided after the image read period in an one-frame period according to the rise of the first vertical synchronization signal may be used.

According to the above-described first embodiment of the disclosure, the timing controller 511 generates the second vertical synchronization signal such that the timing of end of the illumination light that is emitted by the light source device 8 and the start timing at which the reader 202b starts reading an electric signal match. Alternatively, for example, the second vertical synchronization signal may be generated such that the timing of end of the illumination light that is emitted by the light source device 8 and the start timing at which the reader 202b starts reading an electric signal from the light receiver 202a overlap or the second vertical synchronization signal may be generated such that an interval of a constant time (for example, a predetermined pulse) is made. Needless to say, the timing controller 511 may generate the second vertical synchronization signal such that the timing at which the reader 202b starts reading an electric signal from the light receiver 202a is in the period in which the illumination light that is emitted by the light source device 8 is on.

Second Embodiment

A second embodiment of the disclosure will be described below. The second embodiment has the same configuration as that of the endoscope system 1 according to the first embodiment and is different in operations in the low-illuminance mode. Specifically, in the above-described first embodiment, the timing controller 511 generates the second vertical synchronization signal such that the timing of end of the illumination light that is emitted by the light source device 8 and the timing at which the reader 202b reads an electric signal from the light receiver 202a (timing of end of the exposure period) match and transmits the second vertical synchronization signal to the imaging controller 21. In the second embodiment, the timing controller generates the second vertical synchronization signal such that timing of start of illumination light that is emitted by the light source device and end timing at which the reader ends reading an electric signal from the light receiver (timing of start of the exposure period) match and transmits the second vertical synchronization signal to the imaging controller. Thus, operations executed by the endoscope system according to the second embodiment in the low-illuminance mode will be described below. The same components as those of the endoscope system 1 according to the above-described first embodiment are denoted with the same reference numbers of the first embodiment and description thereof will be omitted.

Operation Timing of Endoscope System

Figure 7:
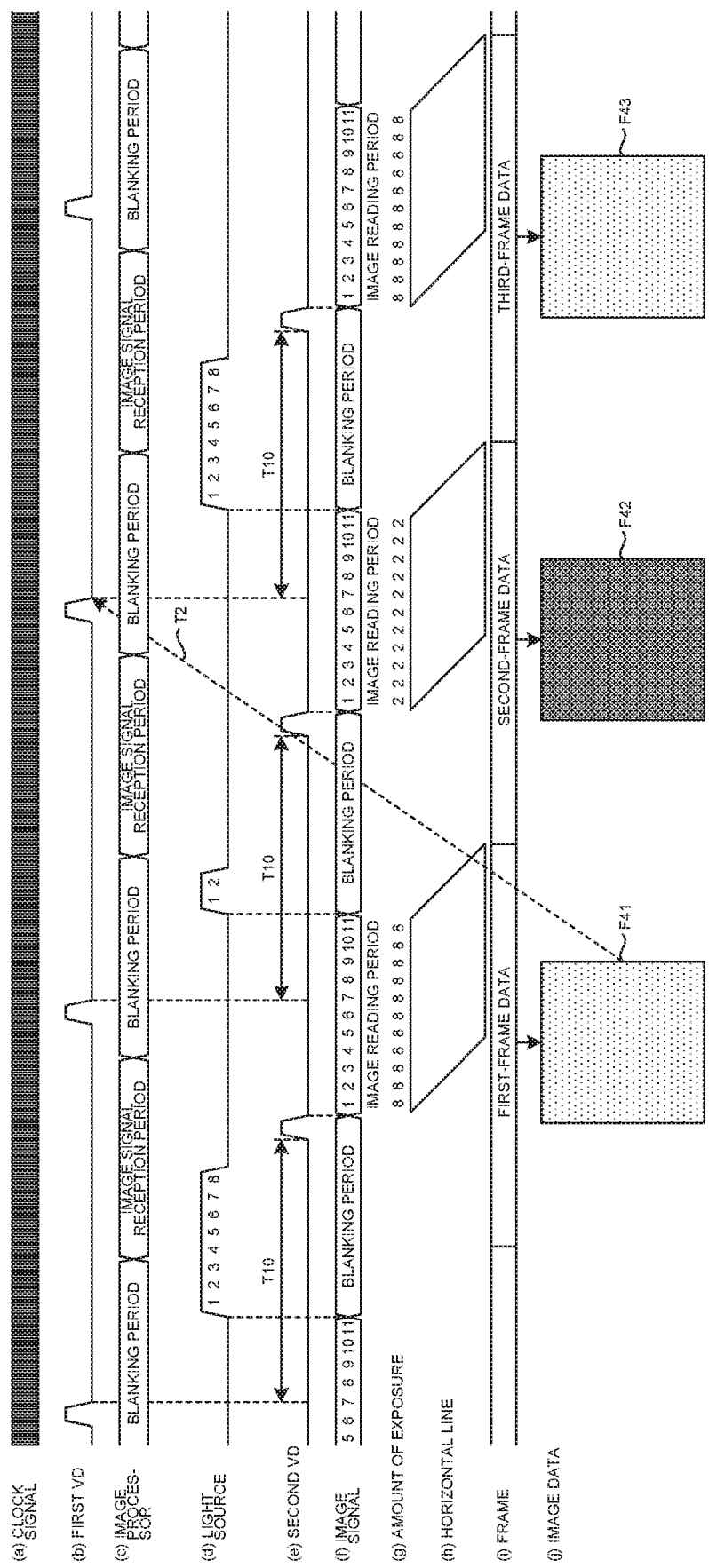
FIG. 7 is a diagram illustrating a timing chart schematically representing operations performed when an endoscope system according to a second embodiment of the invention is in the low-luminance mode.

Operation timing of the endoscope system 1 according to the second embodiment will be described. FIG. 7 is a diagram illustrating a timing chart that schematically represents operations of the endoscope system in the low-illuminance mode. In FIG. 7, from the top, (a) represents a clock signal, (b) represents timing of a first vertical synchronization signal (first VD), (c) represents operations of the image processor, (d) represents timing of light adjustment performed by the light source, (e) represents a second vertical synchronization signal (second VD), (f) represents timing of reading an image signal, (g) represents amounts of exposure of pixels, (h) represents timing of reading pixel horizontal lines, (i) represents timing of frames of image data and (j) represents images of image data. FIG. 7 will be described, assuming that there are 11 horizontal lines.

As illustrated in FIG. 7, based on a first vertical synchronization signal, a clock signal and reference timing of exposure with illumination light that is emitted by the light source device 8, which are input from the timing generator 61, the timing controller 511 generates a second vertical synchronization signal for controlling the timing at which the reader 202b reads an electric signal from the light receiver 202a. Specifically, as illustrated in FIG. 7, the timing controller 511 generates the second vertical synchronization signal such that the reader 202b ends reading an electric signal from the light receiver 202a ends at a time point that is delayed by a predetermined time T10 with respect to the first vertical synchronization signal, which is a time point when the illuminator 22 starts lighting (start timing). More specifically, the timing controller 511 generates the second vertical synchronization signal based on the first vertical synchronization signal such that the timing of start of illumination light that is generated by the illuminator 22 and the end timing at which the reader 202b ends reading an electric signal from the light receiver 202a (timing of start of exposure) match. In other words, the timing controller 511 generates the second vertical synchronization signal that is delayed by the time T1 with respect to the first vertical synchronization signal such that the light source device 8 is able to perform exposure in the all-pixel exposure period of the imaging element 202 when emitting a small amount of light.

Accordingly, in the first frame data, the imaging controller 21 causes the reader 202b to sequentially read image data from the light receiver 202a in the period in which the illuminator 22 is off according to the second vertical synchronization signal and the clock signal that are input from the timing controller 511. Specifically, the imaging controller 21 causes the reader 202b to end reading image data from the light receiver 202a before the illuminator 22 starts emitting illumination light. As a result, the amount of exposure of each horizontal line of the light receiver 202a (the exposure amount is "8") is equalized and the illumination light generated by the illuminator 22 is not applied during a video reading period and this enables generation of an image F41 without luminance. The transmission controller 512 cause the transmitter 514 to transmit the image data of the image F41, which is recorded in the image data recorder 513, in synchronization with the first vertical synchronization signal T2 of the next frame. Accordingly, even when the vertical synchronization signals of the endoscope 2 and the processor 6 are different from each other, the transmitter 514 transmits the image data at the timing corresponding to the first vertical synchronization signal of the processor 6, thereby enabling appropriate image processing in the processor 6.

As illustrated in FIG. 7, in the second frame data, the timing controller 511 generates the second vertical synchronization signal based on the first vertical synchronization signal, the clock signal and the reference timing of exposure with illumination light that is emitted by the light source device 8, which are input from the timing generator 61, such that the reader 202b ends reading an electric signal from the light receiver 202a at the time point when the illuminator 22 starts lighting (start timing). Specifically, the imaging controller 21 causes the reader 202b to end reading image data from the light receiver 202a before the illuminator 22 starts emitting illumination light. As a result, the amount of exposure (the exposure amount is "2") of each horizontal line of the light receiver 202a is equalized and the illumination light that is generated by the illuminator 22 is not applied during the video reading period and this enables generation of an image F42 without luminance. Furthermore, as represented in the image F41, the image F42 and an image F43 represented in FIG. 7, even when the amount of light (period) in PWM light adjustment performed by the light source device 8 changes per frame of image data, no luminance difference occurs. As described above, images having no luminance difference are generated in the low-luminance mode.

Furthermore, according to FIG. 7, the transmission controller 512 causes the image data recorder 513 to temporarily record image data that is read per horizontal line from the reader 202b and, based on the first vertical synchronization signal that is input from the timing generator 61 via the timing controller 511, causes the transmitter 514 to transmit the image data that is recorded temporarily in the image data recorder 513. Accordingly, even when the timing of the first vertical synchronization signal of the processor 6 and the timing of the second vertical synchronization signal of the endoscope 2 differ from each other, it is possible to transmit the image data at timing corresponding to the processor 6 and this enables interchangeability between the processor 6 and the endoscope 2.

According to the above-described second embodiment of the disclosure, based on the first vertical synchronization signal, the clock signal and the reference timing of exposure with illumination light that is emitted by the light source device 8, which are input from the timing generator 61, the timing controller 511 generates the second vertical synchronization signal for controlling timing at which the reader 202b reads an electric signal from the light receiver 202a. Accordingly, it is possible to prevent occurrence of a luminance difference in an image in the low-luminance mode regardless of the type of the processor 6 to be connected.

According to the second embodiment of the disclosure, the timing controller 511 generates the second vertical synchronization signal based on the first vertical synchronization signal such that the start timing at which the illuminator 22 starts lighting and the end timing at which the reader 202b ends reading an electric signal from the light receiver 202a match. Accordingly, it is possible to prevent occurrence of a luminance difference in an image in the low-luminance mode regardless of the type of the processor 6 to be connected.

According to the second embodiment of the disclosure, the timing controller 511 generates the second vertical synchronization signal such that the start timing at which lighting with illumination light that is emitted by the light source device 8 starts and the end timing at which the reader 202b ends reading an electric signal from the light receiver 202a match. Alternatively, for example, the timing controller 511 may generate the second vertical synchronization signal such that the timing of start of illumination light that is emitted by the light source device 8 and the end timing at which the reader 202b ends reading an electric signal overlap or generate the second vertical synchronization signal such that an interval of a constant time (for example, a predetermined pulse) is made. Needless to say, the timing controller 511 may generate the second vertical synchronization signal such that the end timing at which the reader 202b ends reading an electric signal from the light receiver 202a ends is in the period of lighting with illumination light that is emitted by the light source device 8.

OTHER EMBODIMENTS

In the embodiments of the disclosure, under the control of the processor, the light source device performs PWM light adjustment. Alternatively, pulse number modulation (PNM) may be employed.

In the embodiments of the disclosure, causing the light source to emit in the middle of the period of one frame to perform PWM light adjustment. Alternatively, PWM light adjustment may be performed in synchronization with the first vertical synchronization signal of the processor.

In the embodiments of the disclosure, PWM light adjustment (increasing or decreasing light adjustment width) may be performed based on timing of end of a one-frame period.

In the embodiments of the disclosure, the amount of emission of light of one pulse in PWM light adjustment is stable. Alternatively, the amount of emission of light may be changed.

In the embodiments of the disclosure, it is possible to transmit image data according to the vertical synchronization signal of the processor 6 regardless of the type of the processor 6 to be connected and thus the processor 6 is able to perform image processing and transmit the image data to the display device 7.

In the embodiments of the disclosure, image data is transmitted to a processor (control device) via a transmission cable; however, image data need not be transmitted by wired transmission and image data may be transmitted wirelessly. In this case, image data, etc., may be transmitted to the control device according to predetermined wireless communication standards (for example, Wi-Fi (trademark) or Bluetooth (trademark)). Needless to say, wireless communication may be performed according to other wireless communication standards.

According to the embodiments of the disclosure, the processor (control device) and the light source device are different devices. Alternatively, the control device and the light source device may be formed integrally.

The embodiments of the disclosure have been described by exemplifying the simultaneous-lighting endoscope; however, a sequential-lighting endoscope may be used.

Each of the embodiments of the disclosure is the endoscope that is inserted into the subject. Alternatively, for example, a capsule endoscope or an imaging device that captures images of the subject may be used.

In embodiments of the disclosure, in addition to soft endoscopes (upper and lower endoscopes), medical devices that require electromagnetic compatibility (EMC) measurements, such as a hard endoscope, a paranasal endoscope, an electric scalpel or an examination probe, may be also used.

The disclosure produces an effect that it is possible to prevent occurrence of a luminance difference in an image regardless of the type of a processor to be connected.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an illuminator configured to guide illumination light from a light source capable of emitting the illumination light intermittently and apply the illumination light to an object;
   an imaging element comprising:
      a light receiver comprising multiple pixels configured to receive light and perform photoelectric conversion to generate electric signals, wherein the multiple pixels are arranged in a two-dimensional matrix; and
      a reader configured to sequentially read the electric signals per horizontal line of the two-dimensional matrix from each of the multiple pixels;
   a generator configured to, based on a first vertical synchronization signal that is input from an external processor and that is a reference of timing of end of the illumination light emitted by the light source timing of end of the illumination light and the timing of end of the illumination light, generate a second vertical synchronization signal such that the timing of end of the illumination light and start timing at which the reader starts reading the electric signal match; and
   an imaging controller configured to, based on the second vertical synchronization signal, perform exposure of the imaging element, cause the reader to read the electric signals sequentially in a period in which the illuminator is off.

2. The endoscope according to claim 1, wherein the generator is configured to generate the second vertical synchronization signal that is delayed by a predetermined time with respect to the first vertical synchronization signal.

3. An endoscope comprising:
an illuminator configured to guide illumination light from a light source capable of emitting the illumination light intermittently and apply the illumination light to an object;
an imaging element comprising:
   a light receiver comprising multiple pixels configured to receive light and perform photoelectric conversion to generate electric signals, wherein the multiple pixels are arranged in a two-dimensional matrix; and
   a reader configured to sequentially read the electric signals per horizontal line from each of the multiple pixels;
a generator configured to, based on a first vertical synchronization signal that is input from an external processor and that is a reference of timing of start of the illumination light emitted by the light source timing of end of the illumination light and the timing of start of the illumination light, generate a second vertical synchronization signal such that the timing of start of the illumination light and end timing at which the reader ends reading the electric signal match; and
an imaging controlling configured to, based on the second vertical synchronization signal, perform exposure of the imaging element, cause the reader to read the electric signals sequentially in a period in which the illuminator is off.

4. The endoscope according to claim 1, further comprising:
   a recorder configured to record the electric signals per frame of the imaging element;
   a transmitter configured to externally transmit the electric signals per frame that are recorded by the recorder; and
   a transmission controller configured to transmit the electric signals of one frame that are recorded by the recorder to the transmitter in synchronization with the first vertical synchronization signal.

5. The endoscope according to claim 1, further comprising a detector configured to detect a type of the processor to which the endoscope is connected,
   wherein the generator is configured to generate the second vertical synchronization signal based on the type that is detected by the detector and the first vertical synchronization signal.

6. An endoscope system comprising:
   the endoscope according to claim 1;
   the light source configured to intermittently emit the illumination light; and
   a processor configured to perform predetermined image processing on the electric signals that are generated by the endoscope,
   wherein the light source is configured to perform PWM light adjustment per frame of the imaging element.

* * * * *